United States Patent [19]
Madarasz et al.

[11] Patent Number: 5,871,442
[45] Date of Patent: Feb. 16, 1999

[54] PHOTONIC MOLECULAR PROBE

[75] Inventors: Frank Madarasz; Darell Engelhaupt, both of Madison, Ala.; James Wyly, Bow, N.H.; Joseph Milelli, Redondo Beach, Calif.

[73] Assignee: International Diagnostics Technologies, Inc., Madison, Ala.

[21] Appl. No.: 858,260

[22] Filed: May 19, 1997

Related U.S. Application Data

[60] Provisional application No. 60/024,727 Sep. 10, 1996.
[51] Int. Cl.$^6$ .................................................. A61B 5/00
[52] U.S. Cl. ......................... 600/310; 600/316; 356/364
[58] Field of Search ..................... 600/310, 316, 600/318, 319; 356/364, 366, 367

[56] References Cited

U.S. PATENT DOCUMENTS

| | | |
|---|---|---|
| 3,958,560 | 5/1976 | March . |
| 4,223,680 | 9/1980 | Jobsis . |
| 4,266,554 | 5/1981 | Hamaguri . |
| 4,281,645 | 8/1981 | Jobsis . |
| 4,714,080 | 12/1987 | Edgar, Jr. et al. . |
| 4,882,492 | 11/1989 | Schlager . |
| 4,901,728 | 2/1990 | Hutchison . |
| 4,975,581 | 12/1990 | Robinson et al. . |
| 5,009,230 | 4/1991 | Hutchinson . |
| 5,028,787 | 7/1991 | Rosenthal et al. . |
| 5,068,536 | 11/1991 | Rosenthal . |
| 5,077,476 | 12/1991 | Rosenthal . |
| 5,086,229 | 2/1992 | Rosenthal et al. . |
| 5,115,133 | 5/1992 | Knudson et al. . |

(List continued on next page.)

OTHER PUBLICATIONS

PCT International Publication No. WO 94/05984, Publication Date–Mar. 17, 1994, Internationa Application No. PCT/US93/08319, International Filing Date Sep. 3, 1993, Inventor–Milton R. Kaplan.

Flock et al., onte Carlo Modeling of Light Propagation in Highly Scattering Tissues–II: Comparison with Measurements in Phantom IEEE,, vol. 36, No. 12, Dec. 1989 pp. 1169–1173.

Taitelbaum et al, Approximate Theory of Photon Migration in a Two–Layer Medium, Applied Optics vol. 28, No, 12, 15 Jun. 1989, pp. 2245–2247.

Marbach et al, Comparison of Multiivariate Calibration with PCR and PLS for Glucose Using Infrared Spectra of Human Whole Blood, SpIE vol. 1145 Fourier Transform Spectroscopy (1989), pp. 437–438.

(List continued on next page.)

*Primary Examiner*—Cary E. O'Connor
*Assistant Examiner*—Eric F. Winaker
*Attorney, Agent, or Firm*—David P. Krivoshik; Gibbons, Del Deo, Dolan, Griffinger & Vecchione

[57] ABSTRACT

An opto-electronic device utilizes a band of polychromatic light for quantitative analysis of a target molecule within a mixed specimen. A movable polarizer produces a segmented band of partially polarized polychromatic light from the band of partially polarized polychromatic light. A specimen cell adapted for receiving the mixed specimen transports the segmented band of partially polarized polychromatic light to the mixed specimen. A movable polarizing analyzer is optically coupled to the segmented band of partially polarized polychromatic light exiting the mixed specimen. The segmented band of partially polarized polychromatic light before entering the mixed specimen is compared with the segmented band of partially polarized polychromatic light after exiting the mixed specimen. The movable polarizer is synchronized with the movable polarizing analyzer. Additionally a frequency filter can be optically coupled to the movable polarizer, where the frequency filter produces a beam of single frequency ellipitically polarized light from the band of partially polarized polychromatic light such that the segmented band of partially polarized polychromatic light is a segmented band of ellipitically polarized light.

40 Claims, 5 Drawing Sheets

U.S. PATENT DOCUMENTS

| | | |
|---|---|---|
| 5,146,091 | 9/1992 | Knudson . |
| 5,209,231 | 5/1993 | Cote et al. . |
| 5,267,152 | 11/1993 | Yang et al. . |
| 5,277,181 | 1/1994 | Mendelson et al. . |
| 5,313,941 | 5/1994 | Braig et al. . |
| 5,362,966 | 11/1994 | Rosenthal et al. . |
| 5,370,114 | 12/1994 | Wong et al. . |
| 5,383,452 | 1/1995 | Buchert . |
| 5,398,681 | 3/1995 | Kupershmidt ............................ 600/316 |
| 5,452,717 | 9/1995 | Branigan et al. . |
| 5,459,317 | 10/1995 | Small et al. . |
| 5,492,118 | 2/1996 | Gratton et al. . |
| 5,515,847 | 5/1996 | Braig et al. . |
| 5,519,208 | 5/1996 | Esparza et al. . |
| 5,553,616 | 9/1996 | Ham et al. . |
| 5,574,283 | 11/1996 | Quintana . |
| 5,687,721 | 11/1997 | Kuhls ..................................... 600/316 |

OTHER PUBLICATIONS

Ward, et al, Quantitative Infrared Spectroscopy of Glucose in Blood Using Partial Least–Squares Analyses, SPIE vol. 1145 Fourier Transform Spectroscopy (1989), pp. 607–608.

Kellner, Development and Performance of a Novel Ir–Atr–Based Glucose Sensor System, SPIE vol. 1145 Fourier Transform Spectroscopy (1989), pp. 134–137.

Schmidt et al, Multilayer Model of Proton Diffusion in Skin,. Soc. Am. A. vol. 7, No. 11/Nov. 1990, pp. 2141–2153.

Dayan, et al, Photon Migration in a Two–Layer Turbid Medium a Diffusion Analysis, Journal of Modern Optics 1992, vol. 39, No. 7, pp. 1567–1582.

Ward et al, Post–Prandial Blood Glucose Determination by Quantitative Mid–Infrared Spectroscopy Applied Spectroscopy, vol. 46, No. 6, 1992, pp. 959–965.

Haaland et al, Reagentless Near–Infrared Determination of Glucose in Whole Blood Using Multivariate Calibration, Applied Spectroscopy, vol. 46, No.10, 1992, pp. 1572–1578.

Marbach et al, Noninvasive Blood Glucose Assay by Near–Infrared Diffuse Reflectance Spectroscopy of the Human Inner Lip, Applied Spectroscopy, vol. 47, No. 7, 1993, pp. 875–881.

Zhou et al, Sensitive Detection of Optical Rotation in Liquids by Reflection Polarimetry, American Institute of Physics,, Rev. Sci Instrum 64(10), Oct. 1993, p. 28012807.

Heise et al, Effect of Data Pretreatment on the Noninvasive Blood Glucose Measurement by Diffuse Reflectance NIR Spectroscopy, SPIE, vol. 2089, Jul. 1994 pp. 114–115.

Maier, et al, Possible Correlation Between Blood Glucose Concentration and the Reduced Scattering Oefficient of Tissues in the Near Infrared, Optical Society of American Vol. 19, No. 24/Dec. 15, 1994, pp. 2062–2064.

Aronson, Boundary Conditions for Diffusion of Light, Optical Society of America, vol. 12\No. 11/Nov. 1995, pp. 2533–2540.

Bigio et al, Noninvasive Identification of Bladder Cancer with Sub–Surface Backscattered Light SPIE, vol. 2135, 0–8194–1430–Jan. 1994, pp. 26–35 Jan. 1994.

Kohl, et al, Glucose Induced Changes in Scattering and Light Transport in Tissue Simulating Phantoms SPIE, vol. 2839, 0–8194—1736–X95, pp. 780–788. 1995.

Qu et al, The Effect of Physiological Factors and Other Analytes on the Determination of Glucose Concentration in Vivo by Optical Absorption and Scattering Measurements, SPIE, vol. 2679,8194—2053–0/96, pp. 236–242. 1995.

Chung et al, Simultaneous Measurements of Glucose, Glutamine, Ammonia, Lactate, and Glutamate in Aqueous Solutions by Near–Infrared Spectroscopy, Applied Spectroscopy, Vol. 50, No. 2, 1996, pp. 270–276.

Nafie, Vibrational Optical Activity, Focal Point, vol. 50, No. 5, 1996, pp. 14A–26A.

Polavarapu et al, Measurement of Vibrational Circular Dichroism Below –600 $cm^{-1}$ Progress Towards Meeting the Challenge, Applied Spectroscopy, vol. 50, No. 5, 1996, pp. 686–692.

Zawicki, et al, Amperometric Biosensors for Determination of Glucose, Maltose and Sucrose SPIE, vol. 2634, 0–8194—1999–095, pp. 179–183. 1995

INCIDENT LIGHT

α-ANGULAR DISPLACEMENT

TRANSMITTED LIGHT

α-ANGULAR DISPLACEMENT

PHOTONIC MOLECULAR PROBE

CROSS REFERENCES TO RELATED APPLICATIONS

This application claims the benefit of U.S. Provisional application Ser. No. 60/024,727, filed on Sep. 10, 1996.

FIELD OF THE INVENTION

This invention relates generally to the quantitative determination of optically active substances, and more particularly to using polychromatic light for quantitative determination of optically active substances.

BACKGROUND OF THE INVENTION

Monitoring the levels of various chemical agents in human serum is important in the treatment and control of diseases as well as in law enforcement.

Diabetes mellitus is a chronic disease which requires monitoring of blood glucose for proper control. Repetitive determination monitoring of blood glucose is necessary to adequately provide controlled insulin dosing. Currently accurate monitoring is available only by taking and analyzing a blood sample. This invasive procedure is time consuming and not practical for continuous monitoring.

Measurement procedures in law enforcement, including those for intoxication with alcohol, currently utilize indirect tests such as a breath analyzer, motor coordination tests, or require a blood sample. The drawing of a blood sample is an invasive technique which generally necessitates that the blood sample be sent to a laboratory for analysis. Delays in drawing the sample reduce the utility of the test results.

Emergency medical personnel need to be able to immediately, accurately and reliably assess patients' blood levels of both illicit and licit drugs and make confident, correct clinical treatment decisions.

Compliance of the patients with treatment regimes can dramatically improve, and relevant serum level diaries can become easy to maintain by patient or physician where appropriate (e.g., lithium carbonate, tegretol, sodium divalproex, glucose, various hormones, etc.) with an accurate non-invasive quantitative analysis device. In a truly emergent situation "Waiting for the tox-screen to come back" can become a thing of the past, and such acute care treatment can become safer and more reliably appropriate.

The dangers of contacting blood from an individual who is HIV positive or who has Hepatitis are well known. Extreme caution must be taken in drawing and processing the blood samples. Permission of the individual or a court order may be required to obtain the blood sample. Typically, the sample must be drawn by a medically qualified individual. Also, the venipuncture of an immune-compromised individual is, in itself, a risk to that person.

Therefore, there is a need for a non-invasive quantitative determination of substances contained within a person's blood stream.

SUMMARY OF THE INVENTION

In accordance with the present invention, there is provided an opto-electronic device which utilizes a band of polychromatic light for quantitative analysis of a target molecule within a mixed specimen. A movable polarizer produces a segmented band of partially polarized polychromatic light from the band of partially polarized polychromatic light. A specimen cell adapted for receiving the mixed specimen transports the segmented band of partially polarized polychromatic light to the mixed specimen. A movable polarizing analyzer is optically coupled to the segmented band of partially polarized polychromatic light exiting the mixed specimen. The segmented band of partially polarized polychromatic light before entering the mixed specimen is compared with the segmented band of partially polarized polychromatic light after exiting the mixed specimen. The movable polarizer is synchronized with the movable polarizing analyzer. Additionally a frequency filter can be optically coupled to the movable polarizer, where the frequency filter produces a beam of single frequency ellipitically polarized light from the band of partially polarized polychromatic light such that the segmented band of partially polarized polychromatic light is a segmented band of ellipitically polarized light. A method in accordance with the present invention is also described.

BRIEF DESCRIPTION OF THE DRAWINGS

A more complete understanding of the present invention may be obtained from consideration of the following description in conjunction with the drawings in which.

DETAILED DESCRIPTION OF VARIOUS ILLUSTRATIVE EMBODIMENTS

Figure 1A:
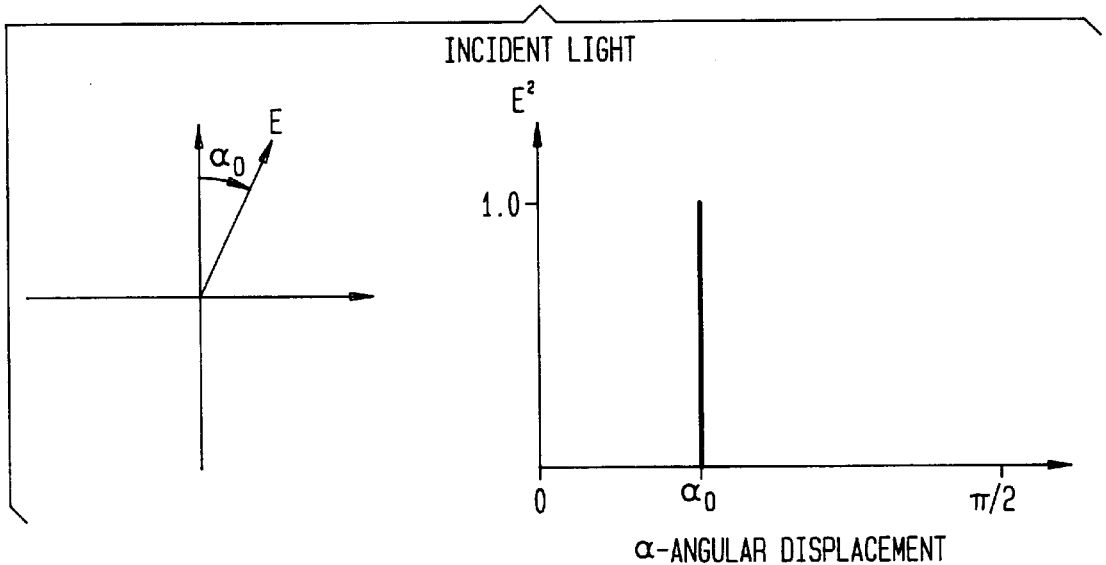
FIGS. 1A and B are a graphical illustration of pure Optical Rotatory Power on a plane polarized wave passing through a chiral sample.

The present invention Photonic Molecular Probe (PMP) is a non-destructive/non-invasive monitoring device, capable of probing and unambiguously identifying quantitatively a target molecule within a mixed specimen. Because the operational capabilities incorporate several physically distinct modes of operation the Photonic Molecular Probe has a myriad of potential applications.

Although the present invention is particularly well suited with monitoring blood constituents such as alcohol, glucose and triglycerides, hormones and drugs and shall be described in this application, the present invention is equally well suited for use in food inspection, plastic waste disposal and continuous alcohol monitoring in brewing vats. The present invention is equally well suited for other production and process operations in which continuous quantitative analysis is advantageous.

The present invention Photonic Molecular Probe is designed to optimize data collection and device miniaturization. It uses state-of-the-art optical and electronic component technology as well as sophisticated data reduction techniques.

The present invention Photonic Molecular Probe operates in a wide spectral region, including, but not limited to, Long Wavelength Infrared to Short Wavelength Infrared and Ultra-Violet, using an elliptical/partially polarized polychromatic (sometimes referred to as chromatically polarized) radiation source. A variety of opto-electronic processes, fundamentally corresponding to basic scattering, processes are utilized to identify the signature and concentration of various target molecules within a mixed specimen with a minimum of data reduction, yielding a highly accurate and cost effective analysis.

The opto-electronic processes include: Absorption; Transmission; Optical Rotatory Power; Circular Dichroism; Reflection and Backscatter; Angular Dependence of The Scattered Beam; Self-Induced Phase Modulation or Heterodyning.

A quantitative basis for an understanding of how polarized light interacts with molecular species having a definite helicity or handedness may be obtained from consideration of Appendix A—Summary of Polarized Light, and of Appendix B—Opitcal Rotation and Circular Dichroism. Optical rotation and circular dichroism are two opto-electronic processes essential in numerous applications of the device. A review of these appendices should make the following discussion of opto-electronic processes and their relationship to the device more transparent.

Absorption and Transmission

Opto-electronic probes typically employed for research and characterization work may indeed use one or more of the measurement processes cited above. They are, however, severely limited in the amount of information they return. This limitation, almost by design, is the result of a very carefully prepared probe beam, generally monochromatic and plane polarized. This probe beam is simple enough to describe quantitatively, is easily characterized experimentally, and under ideal conditions its resulting state upon exiting the sample can be predicted. The interaction of the radiation with certain atoms or molecules which may be present in the sample may cause transitions between atomic or molecular energy eigenstates. The analysis presumes that if a certain atomic or molecular specie is present, then the selection rules for the possible discrete quantum dipole transitions associated with that specie will determine the interactive wavelength of the prepared beam: the transition energy is inversely proportional to the wavelength of the radiation. With a knowledge of the allowable transitions it is then possible to calculate the effect on the incident beam and predict its final state. Theoretically a measurement of absorption or optical rotation on the exiting beam should give enough information to determine the presence of a particular specie of atom or molecule in the sample.

However, under realistic conditions, the radiation can not be purely monochromatic, as there is always a small frequency band about the mean. Moreover, the atom or molecule to be detected does not sit isolated in an isotropic space at zero degrees Kelvin. At elevated temperatures its energy spectrum is broadened, and may be shifted, due to thermal agitation causing fluctuations and the possible introduction of vibronic states. These latter break the symmetry of the structure and allow new transitions to occur. Furthermore, the surrounding constituents in the sample can interact strongly enough with the target specie to perturb its eigenstates, again breaking the molecule's symmetries, splitting them, and further broadening the bands of energies to which transitions may be allowed. Absorption of the beam, now linear and achiral (i.e., a reduction in intensity), or chiral (i.e. a reduction in intensity along with a change of polarization character such as plane to elliptical), will take place over a band of frequencies.

The sensitivity of the measurement may be significantly increased by taking advantage of the wavelength dependence of the light's polarization state. This can be done in one of two ways, each employing a polychromatic source whose frequencies peak (peak referring to the highest intensity) at the frequencies that interact strongly with the target molecule.

The first and most general method is to partially polarize the polychromatic source beam by multiple-reflection techniques. All the wavelength components of the polychromatic light will be polarized, but not in the same way: i.e. the beam, before entering the sample, must be unambiguously optically configured to establish a reference. Each wavelength possesses a dominant polarization character which is in general elliptical. However, due to the nature of the partially polarized light the polarization envelope of the peak frequency is inscribed with a series of spike-like peaks. If the intensity of this light is plotted as a function of the polarization angle there will be a maximum primary peak plus a series of secondary peaks displaced at various angles relative to the primary peak. These secondary peaks act as markers which increase the sensitivity of the probe. Then each wavelength responds differently to a specific optically active medium and each must be examined separately, for it retains its own information about the target. The significance of using a band of partially polarized polychromatic light is that it allows the target molecular system to naturally select out the frequencies with which it interacts strongly. The molecular system acts in a fashion analogous to an optical band-pass filter.

The second method is to select a number of individual frequency components of the polychromatic source, then prepare each component in a purely linear or purely elliptical polarized state thereby building up a set of basis states. The distinction between this procedure and what is normally done with monochromatic plane polarized light is clear: there are simply more frequency components yielding more information. When the target species was chiral, previous methods considered only the optical rotation of one or possibly two frequencies whereas with the present invention Photonic Molecular Probe both optical rotation and circular dichroism are measured over an entire set of basis states.

When the absorption process is linear and achiral the polarization and the wavelength dependence of the polarization are extremely important. Not only will the intensity of each polarization state change differently during the interaction with the target system, but the relative phase shift information contained in each state will also be different. The amount of information available in the emerging beam is enormous.

When the target system is chiral the information from the transmitted beam is many times greater than what can be obtained otherwise.

Optical Rotatory Power and Circular Dichroism

In general, organic molecules are structured in a spiraled form: i.e. they have a definite helicity or handedness. It is this helicity which gives a molecule its ability to rotate the polarization of the incident light. For example, dextrose (d-glucose) is by convention right-handed since, when viewed from the perspective of light emerging from the sample, the polarization axis rotates in a clockwise direction. In contrast, levulose (fruit sugar) is left-handed since it rotates the polarization axis in a counterclockwise direction. Molecules or materials which exhibit this kind of optical activity are said to possess optical rotatory power which is also called optical rotatory dispersion (ORD). Depending upon the action on the polarization of the incident light these are termed dextrorototary and levorotatory respectively.

The magnitude of the angle through which the polarization direction rotates is proportional to the square of the frequency of the incident light. It is also a strong function of the type of material or molecular structure being irradiated. This functional dependence on the physical properties of the medium manifests itself in the difference of the indices of refraction for right-handed and left-handed polarized light, making up the linear polarization state, producing a relative phase shift between the two.

If, however, there is a difference in the absorption between the right-handed and left-handed circularly polarized light making up the polarization state, the phenomenon of circular dichroism is extant. For example if the polarization of the light irradiating the sample were purely elliptical, not only would the ellipse rotate, due to the optical rotatory power, about an axis parallel to the direction of propagation of the light but also the ellipse would distort, that is its eccentricity would change. Both processes generally occur together.

In a fluid, where there is no long-range order aligning the molecules, the molecules are randomly oriented. Nevertheless, the effect of rotatory power is not averaged out to zero. Since the constituent molecules all have a definite helicity, which is the same, they cannot be brought into coincidence with their mirror images: they are said to be enantiomorhpous. More specifically, the molecule cannot have any reflection planes of symmetry or possess inversion symmetry. Thus, the effect of the rotatory power of an individual molecule is enhanced in a fluid state simply because there are now N molecules, regardless of their orientation, contributing to the process. Substances which exhibit both optical rotatory power and circular dichroism are referred to as chiral media.

When partially polarized polychromatic light is transmitted through a chiral medium the primary polarization peak shifts by an amount measured in angular displacement. However, the secondary peaks, each associated with a frequency band about the primary peak, possess their own rotational dynamic, and relative to the primary peak the secondary peaks are now displaced at angles different from those before the light entered the chiral medium.

It should be noted that passing partially polarized polychromatic light directly through a polarizer will average out the secondary peaks referred to above. However, if the beam is chopped before it traverses the polarizer, and appropriately synchronized with the output electronics, the secondary peaks can be recaptured.

Figure 1B:
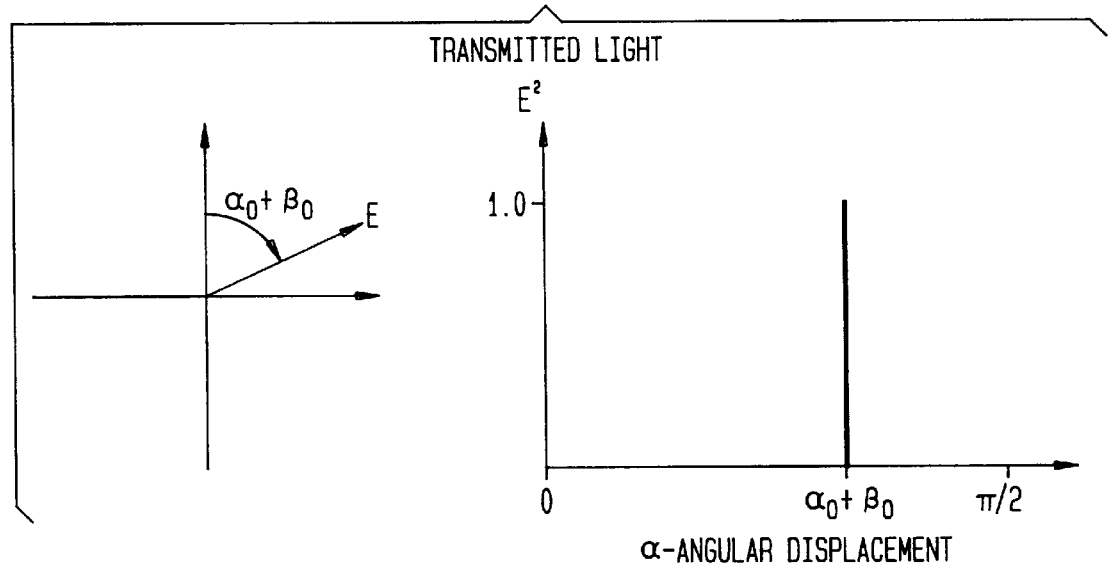
Figure 2A:
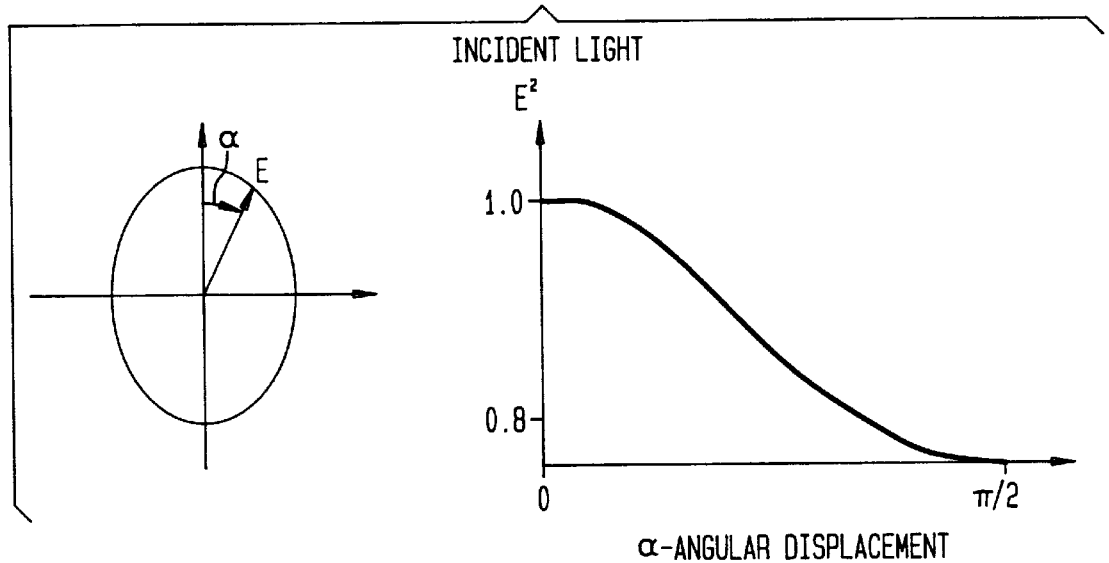
FIGS. 2A and B are a graphical illustration of Optical Rotatory Power and Circular Dichroism on an Elliptically Polarized Wave passing through a chiral sample.
Figure 2B:
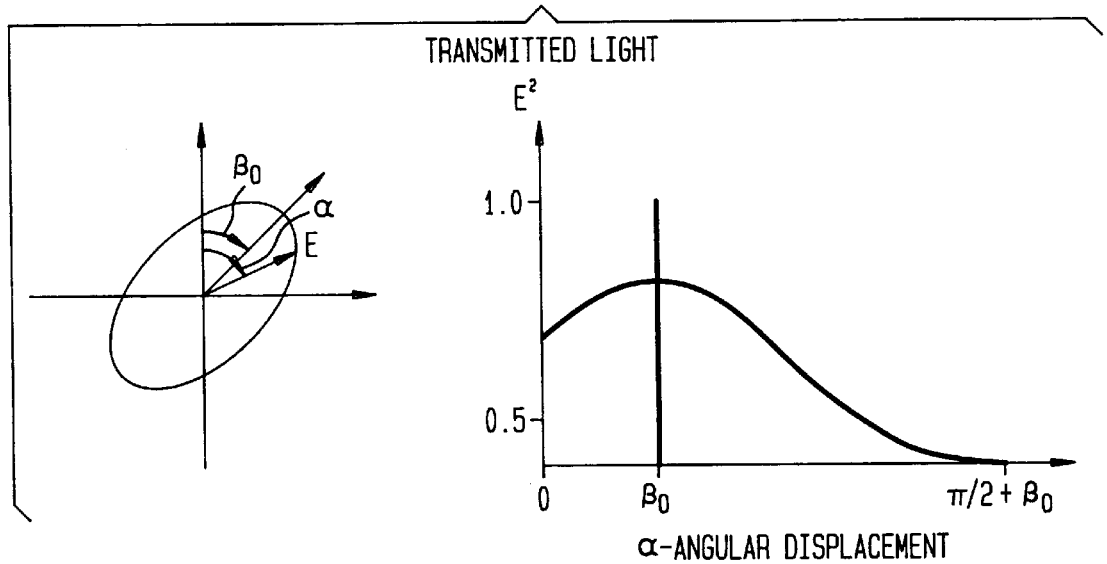
Figure 3A:
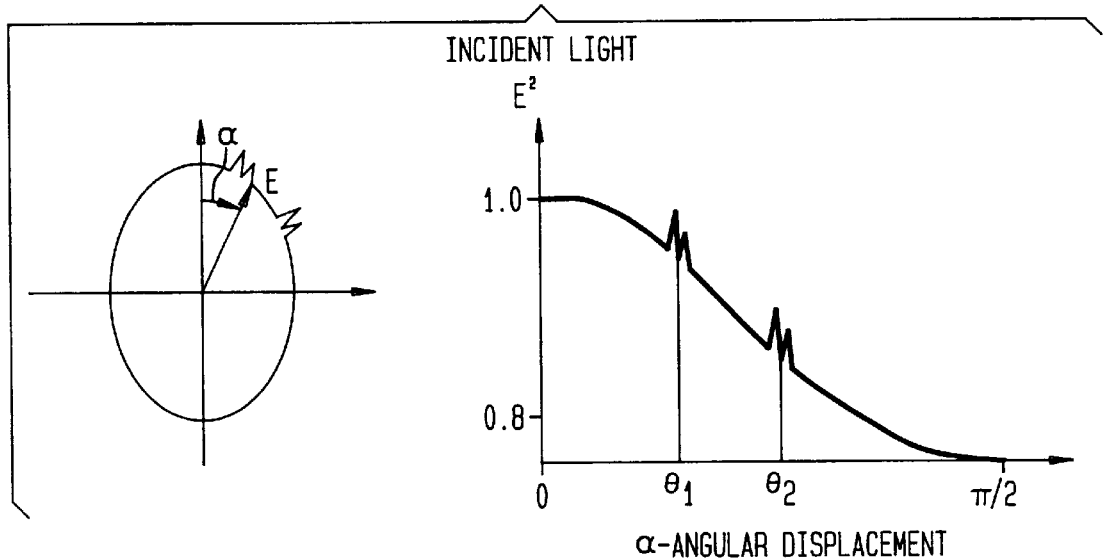
FIGS. 3A and B are a graphical illustration of Optical Rotatory Power and Circular Dichroism on a Chromatic Polarized Wave passing through a chiral sample.

Referring to FIGS. 1A, 1B, 2A, 2B, 3A and 3B there is a graphical illustration in a step-by-step fashion the effects of optical rotatory power, circular dichroism, and partial polarization which are established references. Referring to FIGS. 1A and B there is shown a graphical illustration of pure Optical Rotatory Power on a plane polarized wave after passing through a chiral material, where FIG. 1A corresponds to incident light and FIG. 1B corresponds to transmitted light. Referring to FIGS. 2A and B there is shown a graphical illustration of the effect of Optical Rotatory Power and Circular Dichroism on an Elliptically Polarized Wave passing through a chiral sample, where FIG. 2A corresponds to incident light and FIG. 2B corresponds to transmitted light. It should be noted that not only does the ellipse rotate, but also the shape of the ellipse, its eccentricity or ellipticity changes. Both effects are functions of wavelength and target structure. Referring to FIGS. 3A and B there is shown a graphical illustration of the effect of Optical Rotatory Power and Circular Dichroism on an a Chromatic Polarized Wave passing through a chiral sample, where FIG. 3A corresponds to incident light and FIG. 3B corresponds to transmitted light. As in the case shown in FIGS. 2A and B, the ellipse rotates and distorts. In addition, however, the secondary peaks, which act as probe markers, shift due to the chromaticity as if they possessed their own rotational dynamic. Again, these effects are functions of wavelength and target structure. The subscript naught on the angles indicates that they are fixed. $\beta_o$ in all the figures represents the effect of the optical rotatory power. In FIGS. 2A, 2B, 3A and 3B, $\in$ represents the eccentricity of the elliptically polarized light, essentially the ratio of the ellipse's semi-minor to semi-major axes. The circular dichroism distorts the shape of the ellipse and thus changes its eccentricity.

Figure 3B:
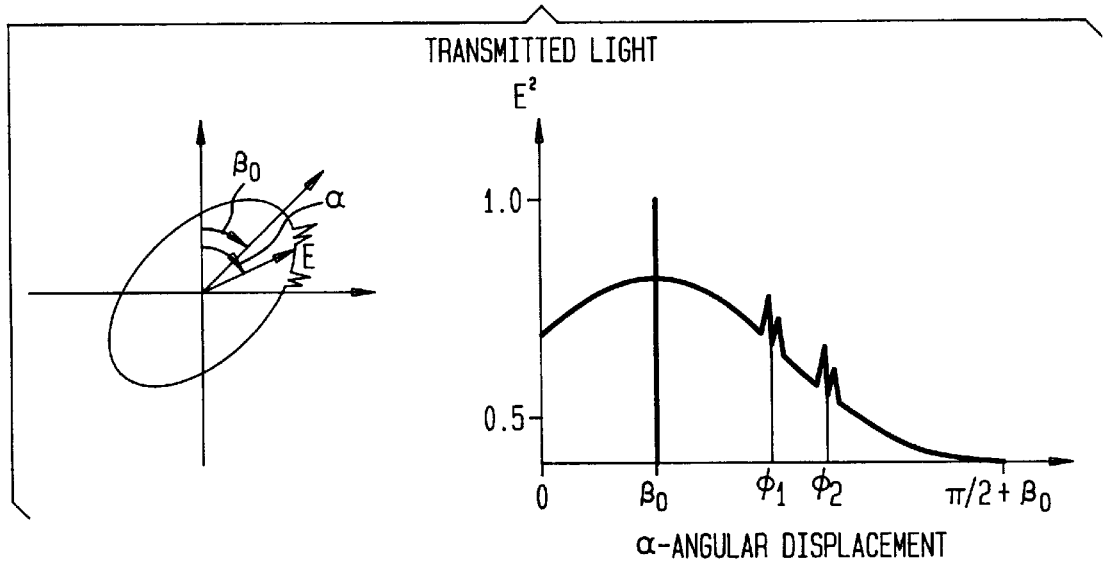

Note that the plots in FIGS. 1B, 2B and 3B are linear representations of the polar information in FIGS. 1A, 2A, and 3A respectively. As alluded to above, sending the configured light represented by FIGS. 1A, 2A, and 3A through a simple rotating analyzer/detector system would modulate the information because of the vector component averaging effect of the analyzer. These plots are intended to illustrate in a step-by-step fashion the information content in a specifically prepared polarization state and the effect on that information after the light is passed through an optically active medium. The present invention Photonic Molecular Probe does not simply modulate the information but is designed to extract the maximum of this information content out of the beam.

Some cases may not require the elaborate approach of chopped light synchronized with the output electronics implicit in the use of partially polarized polychromatic light. Then the use of a set of basis states, each prepared in a purely linear or purely elliptical polarized state, is most advantageous. The result will be a device which has fewer moving components, is more durable and cost effective, and which produces a more readily characterized signal in terms of optical rotation and circular dichroism. The present invention Photonic Molecular Probe is configured to exploit this capability.

Reflection and Backscatter

There are at least two options in defining the optical path through tissue in order to make in vivo real time measurements of substances in human serum. One option is completely traversing a vascular tissue sample, such as a finger, toe, ear lobe, scrotum or labia. If in this mode, for some particular combination of incident light and target specie, it becomes desirable to shield the tissue sample from ambient light the following technique can be used. The source and sensor are both located at the center of tori made from a thin, highly mechanically compliant material. These tori contain a viscous liquid of sufficient amount to ensure a good torus-skin seal, but not so much as to compromise the ability of the thin material to conform to the local skin contours. In this manner an extremely good optical seal may be had much in the same way as some muff-type hearing protectors form an acoustic seal against the head. Another measurement system option can be described for any combination of incident light and target. This option implants an indwelling subcutaneous reflector, such as gold on quartz for the infrared range. This reflector may have any geometric configuration optimal for the intended assay, and may be easily implanted (as are presently various drug delivery systems) in minutes as an office procedure with virtually no trauma. In this alternate technique the path length can be made quite small and be taken through a relatively homogeneous tissue sample. The resulting data will not be very sensitive to small deviations of the flat mirror from being parallel to the plane of the local skin layer. This is because the incident beam and the reflected beam will have a fixed angle between them by virtue of the fixed positions of the source and the detector. The source may also be aligned, using the backscattered halo, such that the incident beam is perpendicular to the reflector.

Angular Dependence of The Scattered Beam

Still more information may be obtained by examining the angular dependence of the scattered beam relative to the incident wave propagation vector. The angular distribution of intensity is frequency dependent. This information is especially useful when working with non-chiral targets. Again the polarization and the wavelength dependence of the polarization are extremely important. Instead of just looking at the intensity of the polarization components in the forward direction it is now possible to look at a two dimensional image of a continuous intensity pattern on a "screen" behind the sample and perpendicular to the incident wave propagation vector.

Heterodyning

In an ideal heterodyne detection system the output signal current (or voltage) is proportional to the strength of the electric field of the optical signal, in contrast to a direct detection system in which the output photocurrent is proportional to the optical signal power. The phase of the optical signal is thus preserved in the output electrical response.

In its simplest form, an optical heterodyne detection system is made up of a highly monochromatic laser field, of frequency $\omega_L$, which serves as a local oscillator field. This field is combined with a monochromatic signal field, of frequency $\omega_S$, through a beam splitter, and then allowed to fall on a photon detector. The photocurrent will then contain a term proportional to $Cos[(\omega_S-\omega_L)t+\phi]$, where t is the time and $\phi$ is the relative phase between the electric field vectors $E_L$ and $E_S$. The difference in the frequencies, $\omega_S-\omega_L$, is called a beat frequency.

The present invention Photonic Molecular Probe operates with partially polarized polychromatic light that peaks at the frequencies that interact strongly with the target molecule. In principle the most intensely peaked frequency can be used as the local oscillator. Then other selected frequencies in the band about it may be used to create a series of different beat frequencies: this process is called self-induced phase modulation. By tracking all the beat frequencies, and hence the relative phases of $E_L$ and $E_S$, in both the incoming and outgoing signals, the phase signature of the target molecule can be obtained.

If the single frequency elliptically polarized light mode of operation is employed a local oscillator beam and a signal beam can be produced by a frequency shift through a pair of acousto-optic modulators, one in each path.

Summary of Physical Properties

While there currently is no complete quantitative theory of optical rotatory power and circular dichroism employing partially polarized polychromatic radiation interacting with matter, the phenomena have been known for over one hundred and fifty years. The basis for at least a qualitative understanding of chromatic polarization is well established.

The Photonic Molecular Probe exploits the response of any one of a myriad of target species to an optical signal prepared in a purposeful manner. Both the dominant frequencies and their polarization states are controlled in the incident beam in a way that anticipates the effect that the target specie (the substance to be assayed) will have.

The Photonic Molecular Probe does not rely soley on the more traditional absorption and transmission processes which represent the present state of the art of an optically based non invasive in vivo assay. The symmetry characteristics exploited by the device design are not limited to those obvious geometrical symmetries long known and studied by stereochemists. Rather they include those less obvious symmetries not directly resulting in, for example, points, lines or planes of reflection symmetry or simple rotational invariances.

Traditional optical analyses using polarized beam probes look simply at uniform first order changes in the polarization states. However, the optical signal exiting the sample carries far more information than that analysis will reveal.

Depending on the embodiment of the Photonic Molecular Probe, and the character of the substance whose concentration is to be measured, the initial beam can be chosen to consist of states of light of linear/elliptical polarization or partially polarized character. Whichever of these incident states is chosen at some point after traversing the sample the optical signal has elliptical polarization character. This allows an extraordinarily noise immune signal to carry the information about substance concentration. Rather than track only amplitude or intensity variations, changes in the angular position of intensity peaks and changes in the polarization ellipse itself are used to extract the data in the Photonic Molecular Probe.

Recently the sophistication of electro-optical technology has made application of these concepts practical. An example of this is the highly evolved state of infrared detectors. Once a target substance is specified, it's unique characteristics are used to craft a highly specialized optical signal, using polarization states, etc., to select the output information needed to detect only that substance.

The present invention Photonic Molecular Probe has flexibility of configuration with the ability to tune to the desired target specie. With a truly achiral molecule RF pumping can be used to induce a form of chirality which makes the molecule in question susceptible to assay.

The performance characteristics of the present invention Photonic Molecular Probe, including accuracy, time stability and others, can be upgraded or degraded as required to provide a "Go/No-Go" gauge, address clinical requirements (typically having three significant digits with no error propagation), or fully configured research instrument. This is accomplished through a certain amount of optional circuit redundancies and enhancements.

Overview of Embodiments

The present invention Photonic Molecular Probe is an opto-electric device which utilizes a band of polychromatic light from a light source for non-destructive/non-invasive quantitative analysis of a target molecule within a mixed specimen. The light beam being emitted from the source is partially polarized, i.e. each wavelength possesses a dominant polarization character, in general elliptical. The pure elliptical character of specific wavelengths may be extracted from the beam by passing the beam through a frequency filter wheel. The resulting elliptical light is then passed through a polarizer which is incrementally rotated in order to segment and to help characterize the shape and orientation of the ellipse. Or, in a more general mode of operation, the frequency wheel is omitted and the beam of partially polarized polychromatic light is directly incident on the polarizer which is incrementally rotated in order to segment and to help characterize the beam structure. A specimen cell is adapted for receiving the mixed specimen and for the traversing of selected segments of the elliptical/partially polarized polychromatic light beam through the mixed specimen. A movable (rotating) polarizing analyzer is set directly in the exiting beam path. The elliptical/partially polarized polychromatic light after exiting the movable polarizing analyzer, is referenced and compared to the elliptical/partially polarized polychromatic light before entering the mixed specimen. The elliptical/partially polarized polychromatic light is composed of frequencies which strongly interact with the particular target molecule.

Illustrative Embodiments

Figure 4:
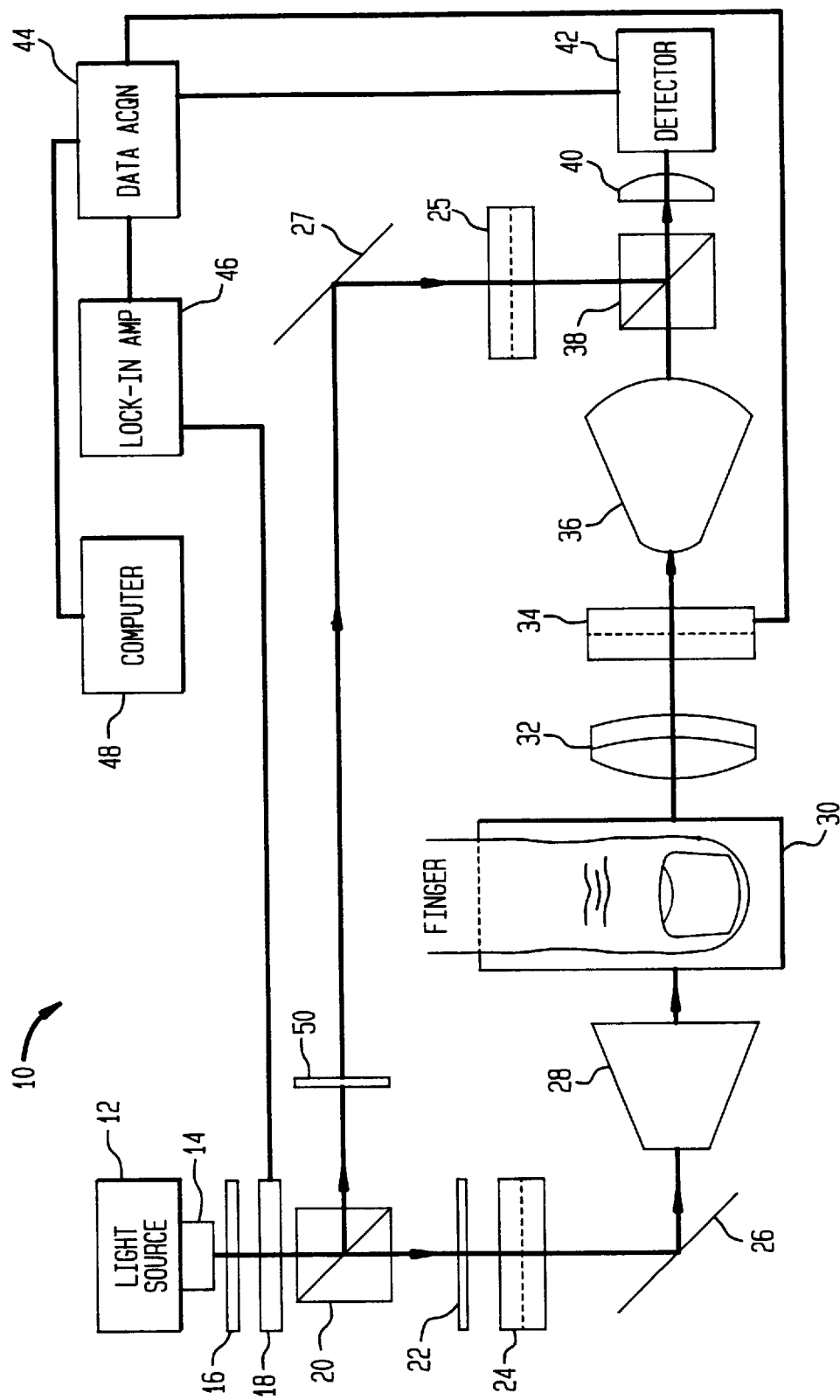
FIG. 4 is a block diagram of a first illustrative embodiment of the Photonic Molecular Probe; and, FIG. 5 is a block diagram of a second illustrative embodiment of the Photonic Molecular Probe.

Referring to FIG. 4 there is shown a block diagram of a first illustrative embodiment of the present invention Photonic Molecular Probe 10.

A light source 12, such as a tungsten filament lamp, is used within an envelope with an internal reflector behind the envelope, similar to a sealed beam head lamp. The envelope contains a halogen gas, usually a mixture of an inert gas such as xenon, and a fluoride or chloride bearing gas. The filament of the light source 12 is typically heated to approximately 2900K and emits, by blackbody emission, in the range 320–2500 nm. For wavelengths longer than about 2500 nm a silicon carbide globar lamp at 1500K is used.

The halogen gas mixture is ionized at the high temperature by the filament, and emits short wavelength spectral lines characteristic of the ionized elements similar to a conventional mercury-inert gas fluorescent lamp. The gas also helps stabilize the temperature effects. With a specialty lamp consisting of both tungsten-halogen and florescent characteristics an advantage in calibration could be realized.

A collimating lens 14, may be a part of the lamp, which contains the light source 12, or may be optically coupled to the lamp. Lamps are available with either focusing or collimating lenses, and internal reflectors which provide a degree of elliptical as well as linear polarization (partial polarization).

A color filter wheel 16 can be used to obtain shorter bandpass frequencies for analyses simplification. The color filter wheel 16 is optically coupled to the collimating lens 14.

Choppers are used in spectrometers principally for one of two reasons: stray light control and double beam operation. In the Photonic Molecular Probe 10 a chopper 18 is optically coupled to the color filter wheel 16. The chopper 18 is electronically coupled to a Lock-in Amplifier 46.

For stray light control the location of the chopper 18 allows timing of a lock-in amplifier 46 to select data which is highly immune to extraneous light. Frequency shifts due to the position of the polarizing elements, and the polarization shift of the selected wavelength, provide quantitative data as the target molecule interacts with the light from the polychromatic source 12. This data is a complex, superimposed non-imaging spectrum, which contains information about retardation, wavelength and amplitude. The use of the chopper 18 can impede the Photonic Molecular Probe's operation by limiting the speed of data collection. However, proper enclosure designs reduce stray light, reflections, and external illumination.

A double beam operation is obtained by inserting a second sample holder between mirror 27 and polarizing element 25, and also replacing polarizing beamsplitter 20 with a reflective version of chopper 18 mounted at 45 degrees to the path between the collimating lens 14 and a half wave plate 22. This unit would be similar to a conventional chopped double-beam instrument. In addition, if desired, the double beam instrument allows for a self calibrating feature by a real-time comparison of known to unknown concentrations of the target specimen: i.e. self-calibration. While double beam operation is useful for an absorbance or transmittance device, timing options of other movable elements offer better choices for a polarization device.

A polarizing beam splitter 20 is optically coupled to the chopper 18. The operation of the Photonic Molecular Probe requires partially polarized polychromatic light to permit markers for the transform analysis. By multiple reflections of a polychromatic beam each frequency becomes partially polarized with a slightly different angular dependence resulting in the a series of markers distributed on an essentially elliptical envelope. A higher degree of polarization can now be obtained by the use of polarizing elements which are minimally affected by lamp aging. By using a broadband beam splitting polarizer a relatively unpolarized light source is split into the S and P polarization states at a 90 degrees exit angle. Additional options include the use of separate polarization devices, such as dichroic polarizers, which are selective at certain wavelengths due to the anisotropic material used.

A half wave plate 22 can be used to control the intensity of the beam to avoid saturation of the detector during calibration or measurements of more nearly transparent materials. The half wave plate 22 is optically coupled to the polarizing beam splitter 20.

A quarter wave plate 50 is used in the reference beam path to control the ellipticity of the beam and also may be used for interference alignment if coherent light is used. The quarter wave plate 50 is optically coupled to the polarizing beam splitter 20.

A polarizer element 24 is optically coupled to the half wave filter 50. The polarizer element 24 is movable and may be dichroic to permit frequency (i.e. wavelength) dependence. The polarizing element 24 is stepped once as an analyzer 34 is incrementally rotated to at least some multiple of 90 degrees. This allows the wavelength dependence of the eccentricity of the polarization ellipse of the partially polarized light through the polarizing beam splitter 20 to be utilized without bandpass filters. An alternative is to use a set of filters at the color filter wheel 16.

If a greater portion of the S polarization state is selected at the polarizing element 24 then the analyzer 34 can be set to transmit the P polarization state to achieve interference at a beam combiner 38.

A first flat mirror 26 is used to direct the partially polarized light to a finger cell 30 through a collimator 28 without chromatic aberration. The reflection at the first flat mirror 26 rotates the polarization 45 degrees counter clockwise while retaining the polarization markers.

A second flat mirror 27 is used to direct the optical output of the quarter wave plate 50 to a second polarizing element 25. The second polarizing element 25 is optically coupled to the beam combiner 38.

A collimator 28 minimizes extraneous scattered light and expand the beam to one of a larger cross-section and lower amplitude, which reduces heating and increases optical interaction with the finger fluids. The collimator 28 can be a reflective device to minimize chromatic effects. The chromatic shift is fixed and can be dealt with in calibration if a lens arrangement is used.

A finger cell 30 can be constructed with cylindrical lenses to optimize the beam path through the finger. While this will affect the polarization it can be used advantageously if a conjugate cylindrical lens is used on the exit side. The light into the finger is partially scattered upon exit. This in turn gives a logarithmic amplitude dependence of light transmitted with respect to cell path length through the sample. Hence by linear collimation and recollection of the scattered light, these lenses minimize problems with varying finger sizes. The intensity of light through the finger is a function of the path length and the concentration of any analyte should be consistent with the normalized intensity. The distance between the cylindrical lenses can be measured as part of calibration to a particular patient. Normalization to other standards, such as water, can also provide accurate calibration. In this case, the amount of analyte divided by the water signal will provide the normalization.

For other embodiments of the present invention the finger cell 30 is generally a specimen cell which is adapted for receiving a particular mixed specimen. While the present invention is particularly well suited for use in non-invasive analysis it is equally well suited for use in the analysis of mixed specimens which may have been collected by an invasive technique as well as specimens which originated from other sources such as a laboratory, production environment or a process operation. Mixed specimens collected by traditional invasive techniques into a vial may be placed into a suitably adapted specimen cell for analysis. Where continuous quantitative analysis is advantageous, such as in a process operation, the specimen cell may be adapted for placement within the operation and may permit the mixed specimen to flow through the specimen cell.

A condensing lens 32 is optically coupled to the finger cell 30 and collects the dispersed light without adding additional depolarization.

The analyzer 34, which is optically coupled to the condensing lens 32, is a movable non-dichroic polarizing element. It is used to track signal variations derived by light intensity versus angular position. The light in this case is partially polarized in a wavelength dependent manner by both the light source 12 and the polarizer element 24. A complete signal is obtained by incrementally moving the analyzer 34 (or electronically scanning a spatial light modulator) through at least 180 degrees. Next, the polarizing element 24 is incremented by a predetermined value, preferably small, to provide a shift in the dichroism and polarization. The analyzer 34 is again scanned at least 90 degrees, or preferably 180 degrees, and the data compared to the previous data.

The difference of data collected when the analyzer 34 is rotated the same 90 degrees (starting position the same), and the polarizing element 24 is stepped, yields phase sensitive differences due to polarization and is influenced by wavelength sensitive dichroism. Another mode of operation is to spin the analyzer element 34 and synchronize an oscilloscope to sweep each half rotation. This will provide a stationary signal. Now the polarizing element is incremented to observe the difference. The data is stored digitally, in columns and rows, for further analysis employing various digital filters. In addition, interferometric data will be produced which can be analyzed with frequency transform methods.

This process can be repeated for positions of the polarizing element 24 to 90 degrees to complete the spectrum. If an opaque beam block is placed between the second mirror 27 and the second polarizing element 25, and no finger is present, then a characteristic signal is achieved for the analyte path. Alternatively, if an opaque block is placed in the cell, then a source calibration is achieved.

A beam reducer 36 can use reflective Cassegrain optics to reduce chromatic shift. Polarization, albeit fixed, is dominant over a lens. The beam reducer is optically coupled between the analyzer 34 and the beam combiner 38.

The optical path between the collimating lens 14 and the analyzer 34 is now crossed with the path between the collimating lens 14 and the second polarizing element 25, producing an initially dark signal at the beam combiner 38, without a chiral sample with no chirality in the finger cell 30. This is because it should be easier to detect small increases in the intensity of light in a dark environment than small decreases in the intensity of light in a bright environment. Note the 45 degree rotation. Furthermore, although the source may not be completely coherent, a coherence path length does exist.

Regardless of whether phase information is collected at separated frequencies by the polarizer element 24, or by any other means, whole blood will yield a very complicated spectrum comprised of a system of superimposed spectra. The polarizer detects primarily phase information.

By using a dual path approach, instead of the partially polarized single path device, two very important goals are achieved.

First, a reference signal is always available for calibration, thereby allowing time-independent calibrations. Furthermore, independence from calibration specific to a given patient becomes a reality, especially with a finger cell 30 that is adjustable.

Second, overlapping Lorentzian absorption bands generate a complex spectrum which can be expressed as an infinite sum of sine and cosine terms. Additionally, information from intensity versus polarizing analyzer position (with sample present) is continuous, and will therefore also have phase sensitive information. One way to handle this massive amount information is to subtract successive intensity data collected throughout the rotation of the analyzer 34 at discrete steps of the polarizer element. This data is combined at the beam combiner 38 with the conjugate polarized original light (S vs. P), yielding interferometric or retardation data. This provides for a real Fourier Transform (or other frequency dependence) instrument. The analysis can be handled similarly to known FTIR spectrometer methods wherein the spectrum is calculated from the interferogram comprised of intensity information from the spectrum of the source minus that of the sample. Since the light is not monochromatic the interferogram is now no longer a simple cosine function.

A forward difference approach may be used to remove large spectral changes and allow observation of the smaller spikes. The application of wavelet theory can be very useful, however the complexity of this task can be reduced by subtraction of intensity data collected at different increments of the polarizer element 24 while rotating the analyzer 34. This then permits true wavelength dependence to be observed and retarded for frequency analysis.

If the polarizing analyzer is rapidly rotated in a continuous fashion, the retardation intensity at the output of a detector 42 versus the position of the polarizing element 24 is a shifting spectrum. The sample information is then derived from successive subtractions of intensity throughout the rotation of the analyzer 34, in any multiple of 180 degrees, plotted against the angular position of the polarizing element 24. As mentioned previously, direct viewing with an oscilloscope is possible by synchronizing in rotation multiples of 180 degrees for each sweep of the oscilloscope.

If the pixel size of the detector 42 is less than the beam diameter from the beam combiner 38 then a condensing lens 40, or focusing lens, can be used by optically coupling the condensing lens 40 between the detector 42 and the beam combiner 38.

The detector 42 can be a single element high speed photo detector diode or photocell having an array of detectors with separate wave length response. A data acquisition system 44 is electrically coupled to the detector 42 and the analyzer 34. An analysis computer 48 is electrically coupled to the data acquisition system 44. For high resolution accuracy a lock-in amplifier 46 is electrically coupled to the chopper 18 and the data acquisition system 44.

Figure 5:
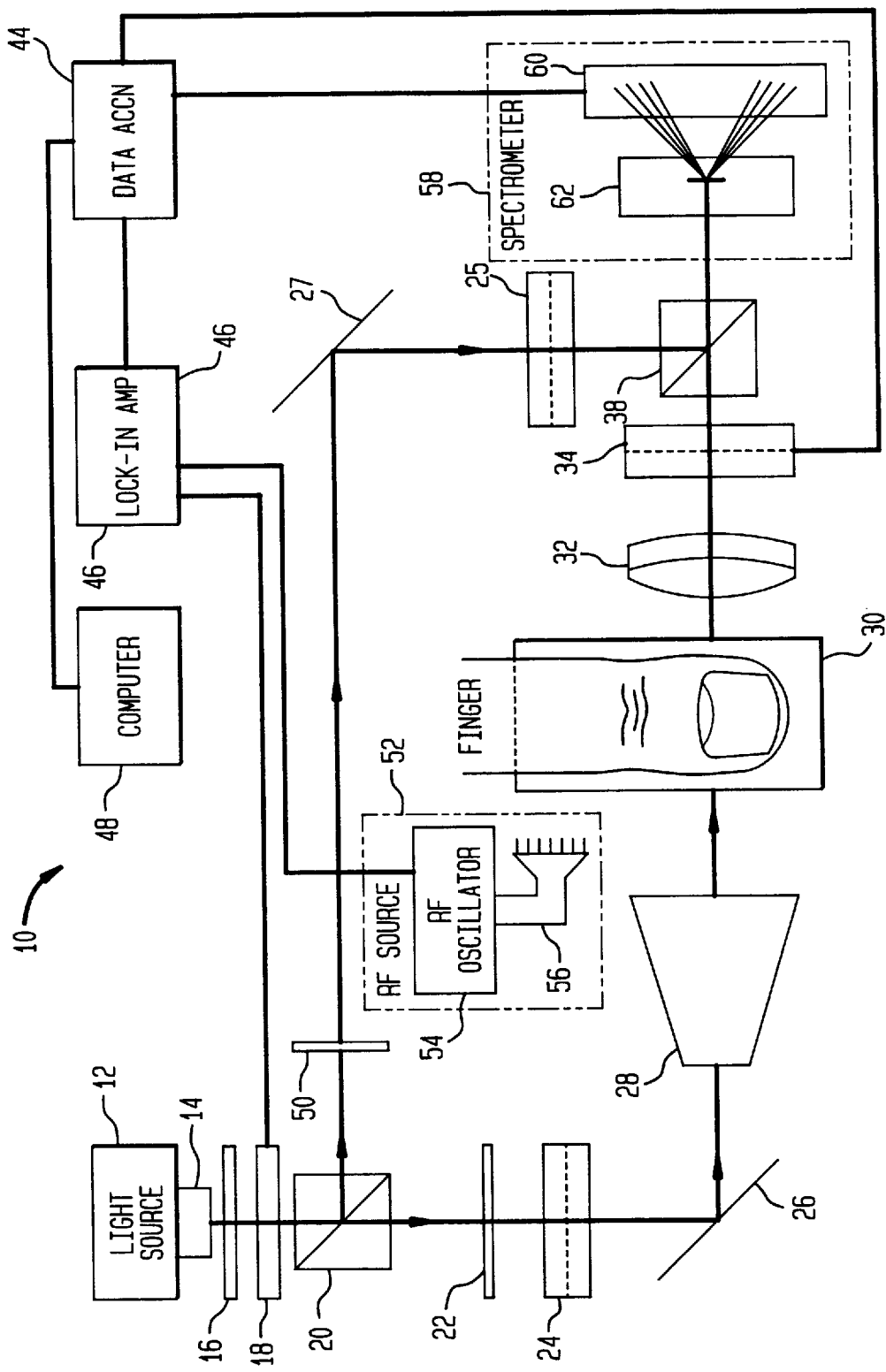

A more versatile instrument is possible by using a small monolithic spectrometer and an array diode to obtain color (or spectral) information similar to FTIR instruments. Referring to FIG. 5, a second illustrative embodiment of the present invention Photonic Molecular Probe which is specifically designed to make possible the assay of substances with no naturally occurring inherent chirality is shown. In this way a snapshot of the spectrum is obtained each time an event signal is triggered. Elements that have similar functions as those is FIG. 4 have been assigned the same reference number and are not again described in detail. For example, each time the polarizing element 24 is incremented, such as when the analyzer is at zero and 180 degrees, a spectrum can be saved. These spectra can then be added for small ranges of the polarizing element 34 known to be specifically active for a particular analyte. Since the spectrum is direct and obtained by a detector array 60 it is not necessary to decompose the retardance data to obtain sample information. An RF source 52 causes directional alignment of certain achiral molecules to assist in detection and identification.

The RF source 52 is electrically coupled to the lock-in amplifier 46 and coupled to the specimen in the finger cell 30. RF source 52 is comprised of an RF oscillator 54 and a resonant coupler 56, such as a coil or dichroic antenna, to excite the molecules during measurement. The output of the beam combiner 38 is optically coupled to a spectrometer 58. The spectrometer 58 is comprised of the detector array 60 and a beam separation element 62, such as a monochrometer. The spectrometer 58 is electrically coupled to the data acquisition system 44.

Additionally, since noise is random, the noise is reduced by the square root of n samples taken and added over the limits of collection and computation. If for example, in the first embodiment of the Photonic Molecular Probe, 3600 data points are collected in the 360 degrees rotation of the analyzer 34, and polarizer element 24 is incremented one degree for each revolution of the analyzer, for 360 degrees, then about 1.3 million data points are rapidly achieved at nominal collection rates. This data can be plotted as the transform of the difference in any two rows of intensity versus position of the analyzer for two corresponding positions of the polarizer element 24. This can alternatively be performed with the second mirror 27 turned or blocked so as to produce a single pass instrument.

With this approach much more versatility is possible from the double pass than from a single pass device. Consider observing retardation data with the second mirror 27 in place. Assume 3600 data points are observed with a Fast Fourier Transform (FFT) taken of the difference of successive rows as the polarizer element 24 increments. For 360 values of the polarizer element 24 then 1.3 million values of retardation are decomposed to a transform spectrum, noting that this spectrum is not a discrete wavelength spectrum but an interferogram source spectrum none the less. A presentation of intensity transform vs. isition of the analyzer 34 and the polarizer element 24 is a 3-D graphical representation of the chiral (and other absorption) interference due to the molecular activity in the finger cell 30. In order to excite polar molecules and molecules of low chiral activity (e.g. some substances other than glucose), it is possible to add the RF source 52. For analysis of very light elements direct current electrophoresis and/or a large magnetic field may also be required, utilizing NMR procedures.

Most FFT procedures use $2^n$ data sets where the abscissa (or rotational position in this case) may be generated once rather than measured. In other words, the angular position is repeated and so it becomes necessary only to count the output control steps rather than measure the actual position of the rotating device. Therefore an analog signal marked by steps of the polarizing element 24 can be stored digitally and, if the rotation is fairly smooth, very good values for angular position could be substituted. With this process values of rotational position not related to direct measurements can be generated: i.e. 4096 data points per revolution ($2^{12}$) for instantaneous response could be synthesized in real time. If it is not possible to achieve the needed rotational correlation exactly enough each time then a high resolution index device is used determine the position of the analyzer 34 and the data acquisition system 44, and the analysis computer 48 becomes the limiting factor of the speed of operation. The lock-in amplifier 46 may be omitted in a portable or lower cost version, however this will be at the cost of some accuracy. Since the data collection at the analyzer 34 is very position (and environment) dependent, the lock-in amplifier 46 needs to synchronize the light blocking function of the chopper 18 and the data acquisition system 44 at rather high speed, especially in a research or laboratory version of the present invention Photonic Molecular Probe where maximum performance is required. Spatial light modulator active optical devices exist which may be substituted for the chopper 18 or the analyzer 34 but presently remain expensive although experimental versions are available.

Other data reduction procedures can be utilized, such as wavelet theory or boxcar methods, which will correlate the small difference signals ideally. Other methods of analyzing blocks of data for optical spectrometers and other instruments are well known to those skilled in the art.

Data Processing Requirements

The specific data processing requirements for the Photonic Molecular Probe will depend upon the sophistication of the device model which can be highly tailored to the specific needs at hand. A significantly degraded (i.e. simplified) version of what is to follow may be sufficient for most applications.

The data collection system in its most general form may be envisioned as consisting of a two dimensional sensor array coupled to the sensors for the angular positions for one or two optical elements in the instrument, all synchronized to the data processing clock either directly or indirectly through another intermediate clock. The sensor array may be frequency (i.e. color) sensitive, and this may prove to provide additional substance characterization information, and possibly further reduce the sophistication needed in the data acquisition of the other parameters mentioned above.

Simplifications in this most general detection system may include collapsing the array to a line or a point, needing only one instead of two positionable optical elements, in addition to others.

While the data processing is done completely on board the Photonic Molecular Probe, the capability of interfacing with external computers exists. The sensed signal is represented by a two dimensional intensity array which, when combined with the information from the polarizing analyzer, contains the crucial angular information previously discussed at length. This signal is highly noise immune. One important observation about this configuration is that the techniques of wavelet transforms and Hadamard transforms may be of great use. This results in a significant reduction in the required computational power, and therefore enhanced possibilities for miniaturization, and portability, and substantially reduced costs. One example of this is in dealing with the two dimensional optical display, in which case the anti resolution, orthogonal, and biorthogonal wavelet transforms can prove quite useful.

Essentially wavelet expansions are just another form of convenient expansions, not unlike Fourier or Hartley transforms, of members of a function space. One unique characteristic is that wavelet transforms map scalar variables into a two dimensional complex domain, and it is this characteristic from which much of their usefulness derives.

The specific wavelet construct to be used in the signal processing will depend on the target molecule and the data acquisition. A general approach to the Photonic Molecular Probe signal processing/discrimination is based on a well known conditional probabilistic reduction method known as Bayes' Rule. The uniqueness of employing the Bayesian method with the Photonic Molecular Probe lies in the fact that very precise physical models can be built directly into the method. For example, atomic form factors, which characterize the electronic structure of various target molecules, can be used for cellular image enhancement. Structure factors (analogues to those used in x-ray diffraction) are another example which characterize the signature of various concentrations of target molecules in solution. The physical models can be all empirical, all theoretical, or a combination of both.

In general then, the expression for the data vector D is given by $$D(\theta)=F(\theta,u)+N(\theta), \quad \text{Equation 1.}$$

where $D(\theta)$ is a function of sampling variable(s) such as polarimeter angle $\theta$, or time t, and $N(\theta)$ is the noise which is assumed to be additive. As with the physical model function, the noise can be represented empirically, theoretically (Gaussian for example), or a combination of both. The physical model function F is then expanded in a set of basis functions $G_j$ containing a set of parameters, such as the concentration of the target molecules in solution, frequencies, decay rates, chirp rates (or any other quantities which may be encountered in the measurement process), collectively denoted by the vector u:

$$F(\theta,V)=\Sigma B_j G_j(\theta,u), \quad \text{Equation 2.}$$

where V=V(B; u). The physical model functions are the atomic form/structure factors, and the basis functions are the appropriately constructed wavelets. The $B_j$ are the associated expansion coefficients.

In the time series problem for example, F would represent the set of functions that would accurately model the time response of the system to an input pulse used as a probe. u could represent frequencies and decay rates characteristic of the system under study. Of interest is the probability of a given value for u which is conditioned on the data D and any prior information, I. This probability, denoted by P(u|DI), is obtained through the use of Bayes' Rule:

$$P(u|DI)=P(D|uI)P(u|I)/P(D|I), \quad \text{Equation 3.}$$

where P(u|I)=prior probability density for u, which summarizes all the prior knowledge on u, and P(D|uI)=likelihood function. An estimate of u can be obtained either by maximizing P(u|DI) with respect to u, or by calculating its first moment:

$$<u>=\int u\, P(u|DI)du. \quad \text{Equation 4.}$$

The second moment, $$<uu>=\int uu\, P(u|DI)du, \quad \text{Equation 5.}$$

gives the correlation on the estimate of u.

In view of the foregoing description, numerous modifications and alternative embodiments of the invention will be apparent to those skilled in the art. Accordingly, this description is to be construed as illustrative only and is for the purpose of teaching those skilled in the art the best mode of carrying out the invention. Details of the structure may be varied substantially without departing from the spirit of the invention, and the exclusive use of all modifications which come within the scope of the appended claim is reserved.

APPENDIX A

Summary of Polarized Light

A general state of polarization of the electric field vector can be formed with the superposition of two linearly plane polarized waves as basis states:

$$E_1=\hat{\epsilon}_1 E_1\, e^{i(k\cdot r-\omega t)},\ E_1=|E_1|e^{i\phi_1}, \quad (A1)$$

and $$E_2=\hat{\epsilon}_2 E_2\, e^{i(k\cdot r-\omega t)},\ E_2=|E_2|e^{i\phi_2}. \quad (A2)$$

In equations A1 and A2 the $\hat{\epsilon}_i$'s are the polarization vectors, the $E_i$'s are the electric field amplitudes, the $\phi_i$'s are the phase angles, and k, r, $\omega$, and t are the wave vector, position vector, circular frequency, and time, respectively.

CASE I Linearly Polarized Light $$\phi_1=\phi_2=\phi,\ |E_1|\neq|E_2|, \quad (A3)$$

$$E=[\hat{\epsilon}_1|E_1|+\hat{\epsilon}_2|E_2|]e^{i(k\cdot r-\omega t+\phi)}. \quad (A4)$$

CASE II Circularly Polarized Light $$|E_1|=|E_2|=E_0,\ \phi_2=\phi_1\pm\pi/2, \quad (A5)$$

$$E=[\hat{\epsilon}_1+\hat{\epsilon}_2\, e^{\pm i\pi/2}]E_0\, e^{i(k\cdot r-\omega t+\phi)}, \quad (A6)$$

$$E=[\hat{\epsilon}_1\pm i\hat{\epsilon}_2]E_0\, e^{i(k\cdot r-\omega t+\phi)}. \quad (A7)$$

The plus (minus) sign is associated with a left- (right-) polarized waves corresponding to circular waves with positive (negative) helicities.

CASE III Elliptically Polarized Light
  Define $$\hat{\epsilon}_\pm = \frac{1}{\sqrt{2}}\ [\hat{\epsilon}_1 \pm i\hat{\epsilon}_2], \tag{A8}$$

then $$E_+ = \hat{\epsilon}_+ E_+ e^{i(k\cdot r - \omega t)},\ E_+ = |E_+|e^{i\phi_+}, \tag{A9}$$

$$E_- = \hat{\epsilon}_- E_- e^{i(k\cdot r - \omega t)},\ E_- = |E_-|e^{i\phi_-}, \tag{A10}$$

$$E = E_+ + E_-, \tag{A11}$$

where $$|E_+| > |E_-|. \tag{A12}$$

A general state of polarization may be formed equally as well with a linear superposition of two circularly polarized waves, of opposite helicity, as basis states.

APPENDIX B

Optical Rotation and Circular Dichroism (The $\mu \cdot m$ Mechanism)

Expressions for both the rotational angle per unit path length, $\delta$, and the change in ellipticity per unit path length, $\Psi$, may be obtained via quantum scattering theory, quantum field theory, or through an application of time-dependent perturbation theory along with the semi-classical theory of radiation. If the pertubation, or interaction potential, is taken as $$H' = -\mu \cdot E - m \cdot H,$$

where E and H are the electric and magnetic fields, respectively, associated with the electromagnetic radiation impinging on the target molecule, and $\mu$ and m are the electric and magnetic dipole moments associated with the target molecule, then the following expressions for optical rotation and circular dichroism may be obtained:

I. Optical Rotation

The rotation per unit path length, of a plane polarized wave, is obtained from the quantum mechanical expression:

$$\bar{\delta}(\omega) = \frac{8\pi}{3\hbar c}\ N\omega^2 \sum_n \frac{Im[<g|\mu|n> \cdot <n|m|g>]}{\omega_{ng}^2 - \omega^2 + i\Gamma_{ng}}, \tag{B1}$$

$$\bar{\delta}(\omega) = \frac{8\pi}{3\hbar c}\ N\omega^2 \sum_n \frac{R_{ng}}{\omega_{ng}^2 - \omega^2 + i\Gamma_{ng}}, \tag{B2}$$

$$R_{ng} = Im[<g|\mu|n> \cdot <n|m|g>], \tag{B3}$$

where $\hbar$ is Planck's constant divided by $2\pi$, c is the speed of light in vacuum, $\omega$ is the frequency of the incident radiation, $\omega_{ng}$ is the transition frequency between states g and n, $<g|\mu|n>$ and $<n|\mu|g>$ are the electric dipole and magnetic dipole transition matrix elements, respectively, between states g and n, N is the number of (non-interacting) molecules per unit volume. And, $\Gamma_{ng}$ is the relaxation or damping parameter between states g and n, which is the full width at half max—FWHM—of the optically active band. Finally, $$[<g|\mu|n> \cdot <n|m|g>] = \mu_{gn} \cdot m_{ng}, \tag{B4}$$

is the inner product between the electric and magnetic dipole moments. Note that the molecule cannot have any reflection planes of symmetry, or possess inversion symmetry. If there were such symmetry, the states g and n would have definite parity with regard to it. Then, selection rules for the operators $\mu$ and m would be of opposite kind with respect to this character ($\mu$ is odd, and m is even) and there would be no states for which the inner product would be different from zero.

$$Re\bar{\delta} = \delta, \tag{B6}$$

$$\delta = 8\pi\ \frac{N}{3\hbar c}\ \omega^2 \sum_n \frac{\omega_{ng}^2 - \omega^2}{(\omega_{ng}^2 - \omega^2)^2 + \Gamma_{ng}^2}\ R_{ng},$$

Clasically, this may be cast in terms of the difference of the indices of refraction of right-handed and left-handed circularly polarized waves which form the basis states of plane polarized wave:

$$\delta = \frac{k}{2}\ [n_R(\omega) - n_L(\omega)], \tag{B7}$$

where $k = \omega/c$ is the magnitude of propagation vector.

II. Circular Dichroism $$\Psi = \frac{8\pi}{3\hbar c}\ N\omega_{ng}^2 \gamma_{ng} \sum_n \frac{R_{ng}}{4(\omega_{ng} - \omega - a)^2 + \gamma_{ng}^2}. \tag{B8}$$

$\gamma_{ng}$ is the full width at half max—FWHM—of the transition and a is a shift in the resonance peak. $\Psi$ is referred to as the ellipticity.

Clasically, $\Psi$ may be cast in terms of the difference of the absorption coeficients of right-handed and left-handed circularly polarized waves which form the basis states of the elliptically polarized wave:

$$\Psi = [\in_R(\omega) - \in_L(\omega)]/4. \tag{B9}$$

What is claimed:

1. An opto-electronic device utilizing a band of partially polarized polychromatic light for quantitative analysis of a target molecule within a mixed specimen, said device comprising:
    a movable polarizer for producing a segmented band of partially polarized polychromatic light from the band of partially polarized polychromatic light;
    a specimen cell adapted for receiving the mixed specimen and for transporting said segmented band of partially polarized polychromatic light to the mixed specimen;
    a movable polarizing analyzer optically coupled to said segmented band of partially polarized polychromatic light exiting the mixed specimen; and
    comparison means for comparing said segmented band of partially polarized polychromatic light before entering the mixed specimen with said segmented band of partially polarized polychromatic light after exiting the mixed specimen,
    wherein said movable polarizer is synchronized with said movable polarizing analyzer.

2. The device as recited in claim 1 further comprising a frequency filter optically coupled to said movable polarizer, wherein said frequency filter produces a beam of single frequency elliptically polarized light from the band of partially polarized polychromatic light such that said segmented band of partially polarized polychromatic light is a segmented band of ellipitically polarized light.

3. The device as recited in claim 1 wherein said band of partially polarized polychromatic light includes frequencies which interact strongly with the target molecule.

4. The device as recited in claim 1 wherein said band of partially polarized polychromatic light comprises infrared light.

5. The device as recited in claim 1 wherein said band of partially polarized polychromatic light comprises ultraviolet light.

6. The device as recited in claim 1 further comprising an RF source coupled to said specimen cell whereby said RF source causes particular changes of selected achiral molecules within the mixed specimen.

7. The device as recited in claim 1 wherein said comparison means further comprises a photo detector.

8. The device as recited in claim 1 wherein said comparison means further comprises a spectrometer.

9. The device as recited in claim 1 further comprising a frequency filter for producing a single frequency elliptically polarized light band from said band of partially polarized polychromatic light.

10. The device as recited in claim 1 wherein said movable polarizer is incrementally rotatable.

11. The device as recited in claim 1 wherein said movable polarizing analyzer is incrementally rotatable.

12. The device as recited in claim 1, wherein said comparison means further comprises a signal processor for determining a quantitative level of the target molecule within the mixed specimen.

13. The device as recited in claim 12, wherein said quantitative level corresponds to a glucose level.

14. The device as recited in claim 12, wherein said quantitative level corresponds to an ethanol level.

15. The device as recited in claim 12, wherein said quantitative level corresponds to a drug serum level.

16. The device as recited in claim 12, wherein said quantitative level corresponds to a hormone serum level.

17. The device as recited in claim 12, wherein said quantitative level corresponds to a triglycerides level.

18. An opto-electronic device utilizing a band of partially polarized polychromatic light for quantitative analysis of a target molecule within a mixed specimen, said device comprising:

a frequency filter for producing a beam of elliptically polarized light from the band of partially polarized polychromatic light;

a polarizer for producing segmented characterized light by rotating said polarizer, said elliptically polarized light optically coupled to said a specimen cell adapted for receiving the mixed specimen so that said segmented characterized light is brought onto and through the mixed specimen;

a movable polarizing analyzer optically coupled to segmented characterized light exiting the mixed specimen; and comparison means for comparing said segmented characterized light before entering the mixed specimen with said segmented characterized light after exiting the mixed specimen, wherein when said polarizer is rotated to a selected position, said movable polarizing analyzer is scanned from a predetermined position through a predetermined range.

19. The device as recited in claim 18 wherein said segmented characterized light includes frequencies which interact strongly with the target molecule.

20. The device as recited in claim 18 wherein said partially polarized polychromatic light comprises infrared light.

21. The device as recited in claim 18 wherein said partially polarized polychromatic light comprises ultraviolet light.

22. The device as recited in claim 18 further comprising an RF source coupled to said specimen cell whereby said RF source causes a state change of selected achiral molecules within the mixed specimen.

23. The device as recited in claim 18 wherein said comparison means further comprises a photo detector.

24. The device as recited in claim 18 wherein said comparison means further comprises a spectrometer.

25. The device as recited in claim 18 wherein said polarizer is incrementally rotatable.

26. The device as recited in claim 18 wherein said movable polarizing analyzer is incrementally rotatable.

27. The device as recited in claim 18, wherein said comparison means further comprises a signal processor for determining a quantitative level of the target molecule within the mixed specimen.

28. The device as recited in claim 27, wherein said quantitative level corresponds to a glucose level.

29. The device as recited in claim 27, wherein said quantitative level corresponds to an ethanol level.

30. The device as recited in claim 27, wherein said quantitative level corresponds to a drug serum level.

31. The device as recited in claim 27, wherein said quantitative level corresponds to a hormone serum level.

32. The device as recited in claim 27, wherein said quantitative level corresponds to a triglycerides level.

33. A method for quantitative analysis of a target molecule within a mixed specimen, said method comprising the steps of:

producing elliptical/partially polarized polychromatic light;

producing segmented characterized light by rotating a polarizer optically coupled to said elliptical/partially polarized polychromatic light;

transporting said segmented characterized light onto and through the mixed specimen;

polarizing said segmented characterized light exiting the mixed specimen; and comparing said segmented characterized light before entering the mixed specimen with said segmented characterized light after exiting the mixed specimen, wherein the step of producing segmented characterized light is synchronized with the step of polarizing said segmented characterized light.

34. The method as recited in claim 33 further comprising the step of determining a quantitative level of the target molecule within the mixed specimen.

35. The method as recited in claim 34, wherein said quantitative level corresponds to a glucose level.

36. The method as recited in claim 34, wherein said quantitative level corresponds to an ethanol level.

37. The method as recited in claim 34, wherein said quantitative level corresponds to a drug serum level.

38. The method as recited in claim 34, wherein said quantitative level corresponds to a hormone serum level.

39. The method as recited in claim 34, wherein said quantitative level corresponds to a triglycerides level.

40. The method as recited in claim 33 further comprising the step of coupling an RF source to the mixed specimen whereby said RF source causes particular changes of selected achiral molecules within the mixed specimen.

* * * * *